US00PP12232P2

(12) United States Plant Patent
Ronald et al.

(10) Patent No.: US PP12,232 P2
(45) Date of Patent: Nov. 27, 2001

(54) LINDEN TREE NAMED 'HARVEST GOLD'

(75) Inventors: Wilbert G. Ronald; James R. Durand, both of Manitoba (CA)

(73) Assignee: Bailey Nurseries, Inc., St. Paul, MN (US)

( * ) Notice: Subject to any disclaimer, the term of this patent is extended or adjusted under 35 U.S.C. 154(b) by 0 days.

(21) Appl. No.: 09/316,129

(22) Filed: May 21, 1999

(51) Int. Cl.[7] ..... A01H 5/00
(52) U.S. Cl. ..... Plt./222
(58) Field of Search ..... Plt./222

*Primary Examiner*—Amy J. Nelson
*Assistant Examiner*—Anne Marie Grünberg

(74) *Attorney, Agent, or Firm*—Burns, Doane, Swecker & Mathis, LLP

(57) ABSTRACT

A new and distinct *Tilia cordata*×*Tilia mongolica* Linden tree cultivar is provided that is excellent for growing as an attractive boulevard tree. The crown is upright and is unlike the crown configuration commonly observed in *Tilia mongolica* Linden trees. The foliage is glossy medium green in the summer and a consistent golden yellow in the fall. Good resistance to leaf gall mites and fungal leaf spotting is exhibited. Attractive exfoliating grey-brown bark is formed on an sturdy trunk as the tree matures. Fragrant flowers are formed on moderate basis and the resulting seed crop is sparse. Good winter hardiness is observed with the tree being well adapted for U.S.D.A. Hardiness Zone No. 3. A high degree of tolerance to winter sunscald damage also is provided.

3 Drawing Sheets

SUMMARY OF THE INVENTION

The original tree of the present invention was discovered and selected while growing among open-pollinated Linden seedlings being grown at Portage la Prairie, Manitoba, Canada. The seeds used to produce the seedlings were obtained from an extremely hardy Littleleaf Linden *Tilia cordata* female parent tree growing at the Morden Research Station, Manitoba, Canada, since about 1942 and were planted during 1980. The seed source for this parent tree (non-patented in the United States) had been obtained in Manchuria in the late 1930's by Dr. Frank Skinner and was considered to be a distinct form of *Tilia cordata*. The male parent of the new cultivar of the present invention is believed to have been a nearby Mongolian Linden *Tilia mongolica* (non-patented in the United States) since the characteristics of the new seedling included golden buds, exfoliating bark, thin leaves, and early fall leaf coloration.

The outstanding qualities of the new cultivar were first observed during 1988. Since that time the new cultivar has been carefully preserved and studied. Had we not discovered and preserved the new cultivar of the present invention it would have been lost to mankind.

It was found that the new *Tilia cordata*×*Tilia mongolica* Linden tree cultivar of the present invention exhibits the following combination of characteristics:

(a) Exhibits an upright crown which renders it particularly well suited for growing in a setting where a reduced crown spread is desired.

(b) Forms attractive glossy medium green foliage during the summer and consistent golden yellow foliage in the fall that displays good resistance to leaf gall mites and fungal leaf spotting.

(c) Forms attractive exfoliating grey-brown bark once the tree reaches a caliper of approximately two inches.

(d) Forms on a moderate basis fragrant flowers and a sparse seed crop, and (e) Exhibits superior winter hardiness and a high degree of tolerance to winter sunscald damage.

It additionally has been observed that gold-colored buds are formed in late summer which turn to reddish-brown during the winter. The inherently upright grown habit reduces the need for the continual staking of budded whips. The hardiness is found to be superior to that of the 'Ronald' Linden (U.S. Plant Pat. No. 8,239). The new cultivar is particularly well suited for growing as an attractive boulevard tree.

The new cultivar of the present invention has been asexually reproduced at Portage la Prairie, Manitoba, Canada beginning in 1988 by budding on Littleleaf Linden *Tilia cordata* rootstock. Such propagation has demonstrated that the combination of characteristics described herein is stable and is successfully transmitted to succeeding generations.

The new *Tilia cordata*×*Tilia mongolica* Linden cultivar of the present invention has been named the 'Harvest Gold' cultivar.

BRIEF DESCRIPTION OF THE PHOTOGRAPHS

The accompanying photographs show, as nearly true as it is resonably possible to make the same in color illustrations of this character typical trees, foliage and bark of the new cultivar. The trees were grown at Portage la Prairie, Manitoba, Canada.

FIG. 1 illustrates during the summer of 1994 the original tree of the new cultivar. The tree age was approximately 14 years, the height was approximately 28 feet, and the caliper was approximately 9 inches.

FIG. 2 illustrate during the summer of 1996 a tree of the new culivar while budded on *Tilia cordata* rootstock. The tree was approximately 8 years of age, the height was approximately 18 feet, and the caliper was approximately 4 inches.

FIG. 3 illustrates during the summer of 1998 typical foliage of the new cultivar formed on a budded tree of the new cultivar having an age of approximately 10 years. The thin glossy medium green coarsely-toothed character of leaves is apparent. The illustrated leaves were approximately 4 inches in length and approximately 4 inches in breadth.

DETAILED DESCRIPTION

Figure 1:
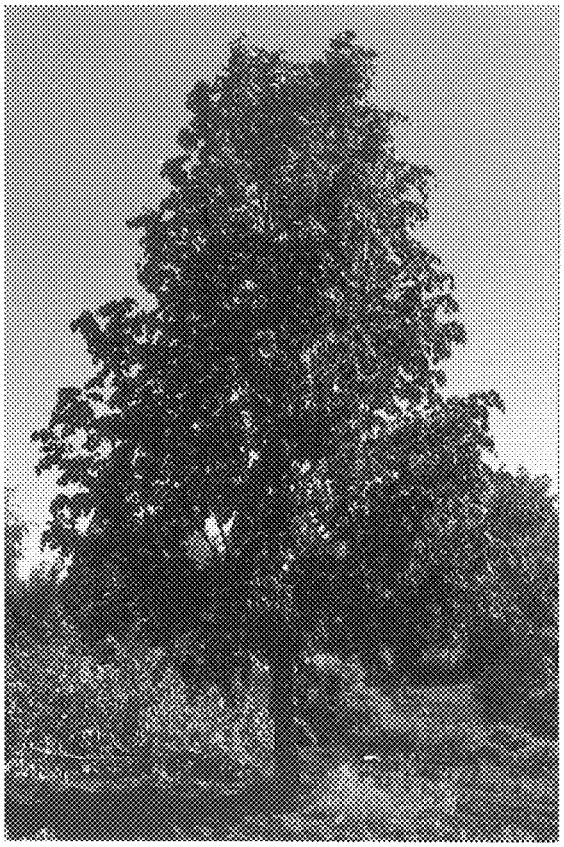
Figure 2:
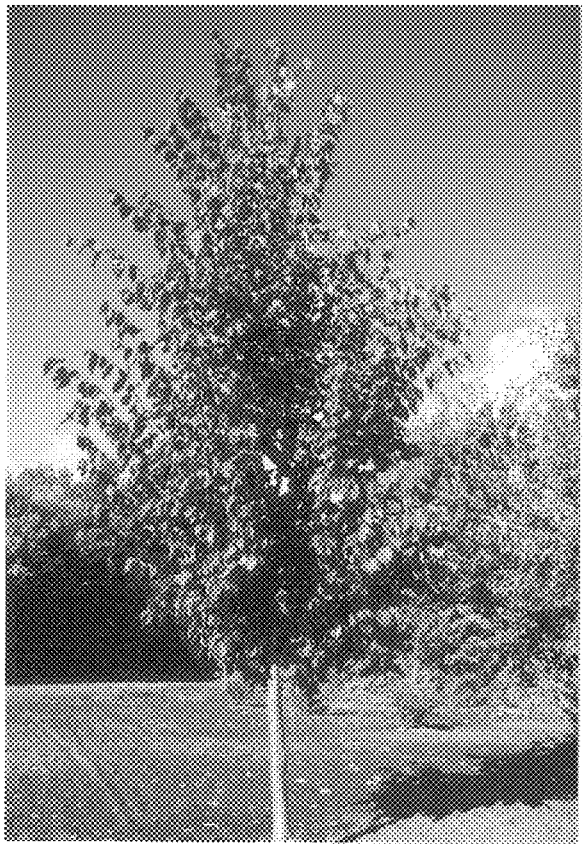

The chart used in the identification of colors is that of The Royal Horticultural Society (R.H.S. Colour Chart). Common terms are to be accorded their ordinary dictionary significance. The description is based upon the growing of trees at Portage la Prairie, Manitoba, Canada. Both the original tree and progeny budded on *Tilia cordata* rootstock were observed and the description is based on such observations. No significant phenotypic differences have been observed between the original tree and the progeny budded on *Tilia cordata* rootstock.

Botanical classification: *Tilia cordata*×*Tilia mongolica*, cv. 'Harvest Gold'.

Plant:

*Growth habit.*—Upright (as illustrated) unlike that commonly associated with *Tilia mongolica*. There commonly is a strong dominant leader upon which are borne sharp-angled branches. The lateral branches commonly are disposed at an angle of approximately 35 degrees to the central leader. This produces an overall upright oval crown configuration. The upright growth habit renders the new cultivar of the present invention an excellent choice whenever a reduced crown spread is desirable. The new cultivar is particularly well suited for growing as a uniform planting along boulevards. An 8 year-old tree typically has a height of approximately 16 feet, a spread of approximately 8 feet, and a caliper of approximately 4½ inches measured 6 inches above the ground. A 15 year-old tree typically has a height approximately 25 feet, a spread of approximately 10 feet, and a caliper of approximately 10 inches measured 6 inches above the ground.

*Size.*—Fully mature trees are projected to obtain a height of approximately 30 to 40 feet and a spread of approximately 25 to 30 feet.

Figure 5:
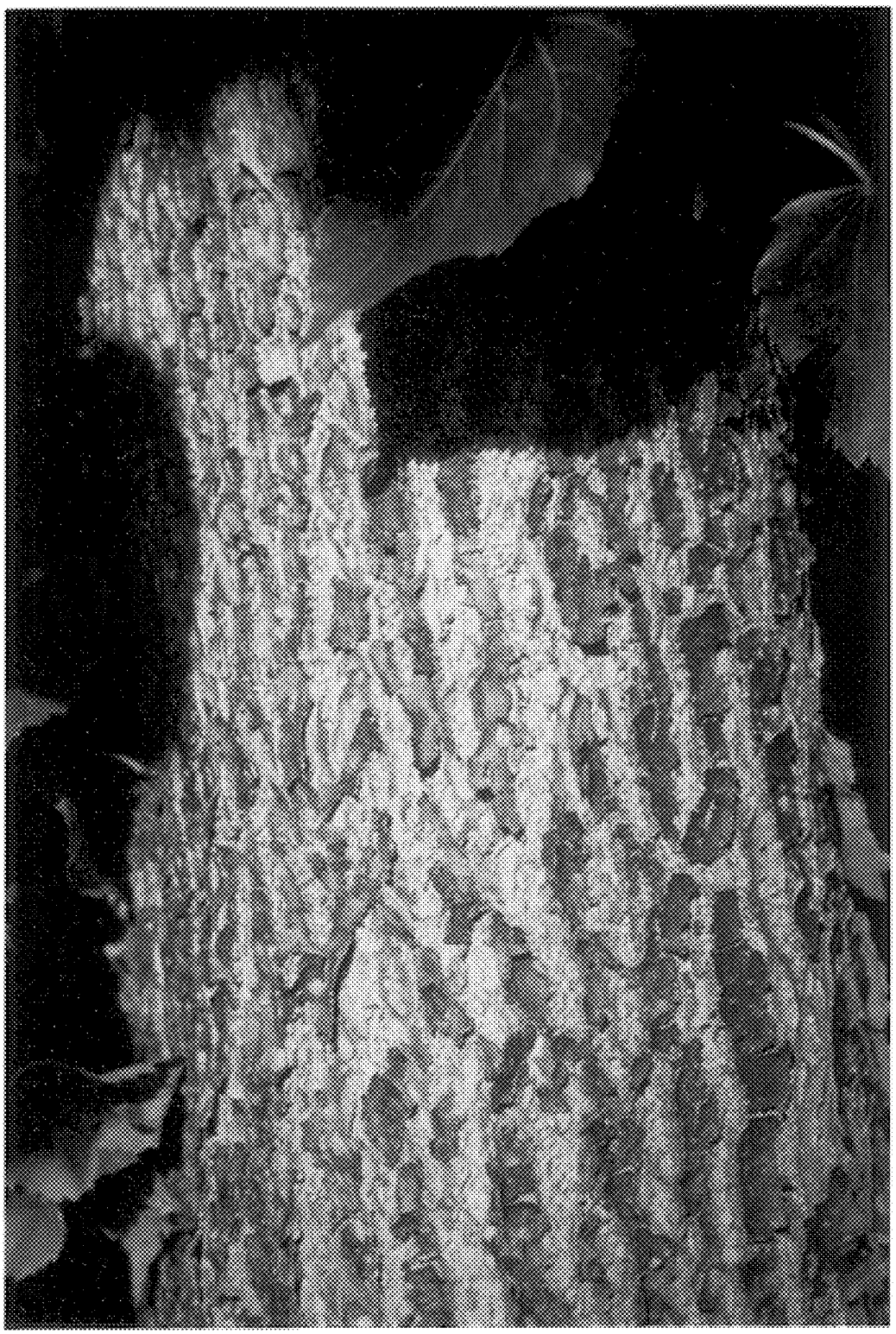
FIG. 5 illustrates during the summer of 1998 the typical bark of the new cultivar formed on a budded tree of the new cultivar having an age of approximately ten years. The exfoliating character of the attractive grey-brown bark is apparent.

*Bark.*—On a 4½ inch caliper tree, the bark is grey-brown (Grey-Brown Group 199D) with some small areas of grey-orange (Grey-Orange Group 165B). On a 12 inch caliper tree, the bark is grey (Black Group 202D) with some small areas of grey-brown (Grey-Brown Group 199D). There is some exfoliation as illustrated in FIG. 5.

*Suckering.*—The tendency to sucker is moderate and is similar to that of the species *Tilia cordata.*

Foliage:

*Timing.*—The leaf-out time is similar to that of the 'Ronald' Linden and commonly occurs at approximately May 15th.

*Form.*—Alternate and somewhat heart-shaped, broadly ovate to rounded, and abruptly-pointed at the tip.

*Leaf length.*—Up to approximately 4 inches.

*Leaf width.13* Up to approximately 4 inches.

*Petiole.*—Greyed-Yellow Group 162C, and approximately 15 mm in length and approximately 1.5 mm in width.

*Lenticles.*—Circular to oblong in configuration, commonly measuring approximately 1/16 inch across, generally white, and commonly bear a line in the middle.

*Leaf margins.*—Coarsely toothed.

Figure 3:
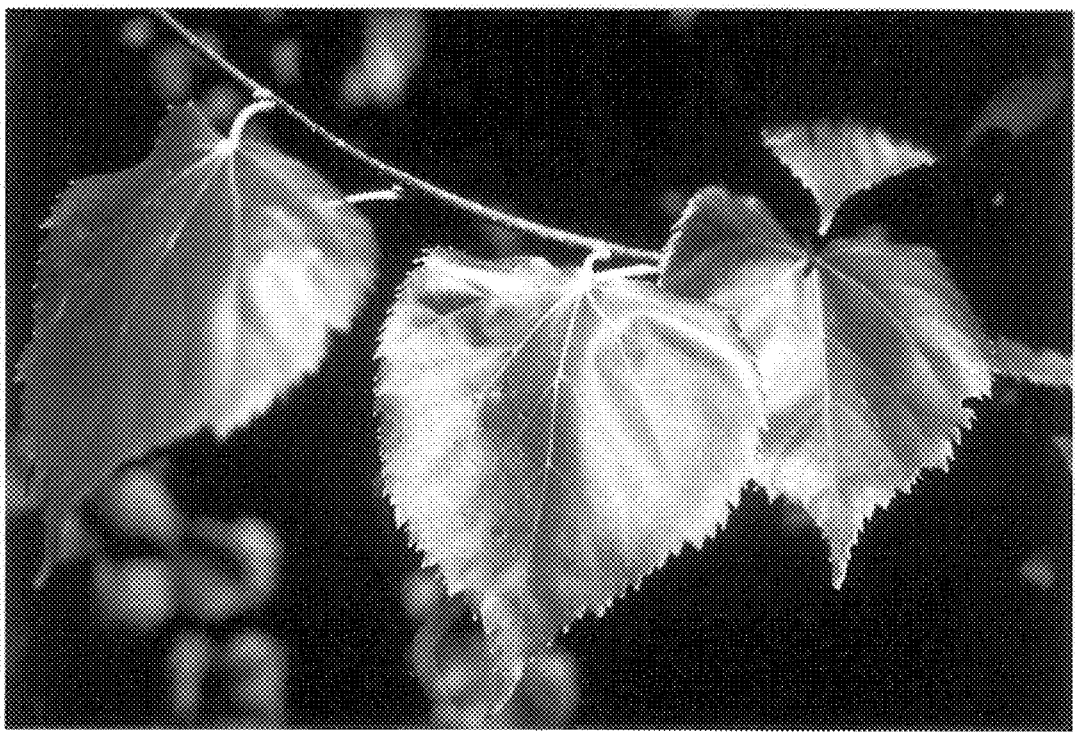

*Summer color.*—Medium Green, Yellow-Green Group 143B (see FIG. 3) on the upper surface, and lighter green, Yellow-Green Group 144D, on the under surface when mature. The vein coloration is Greyed-Yellow Group 162D when mature. The immature leaves are Yellow-Green Group 144A on the upper surface and Yellow-Green Group 147C on the under surface. No leaf glands have been observed.

Figure 4:
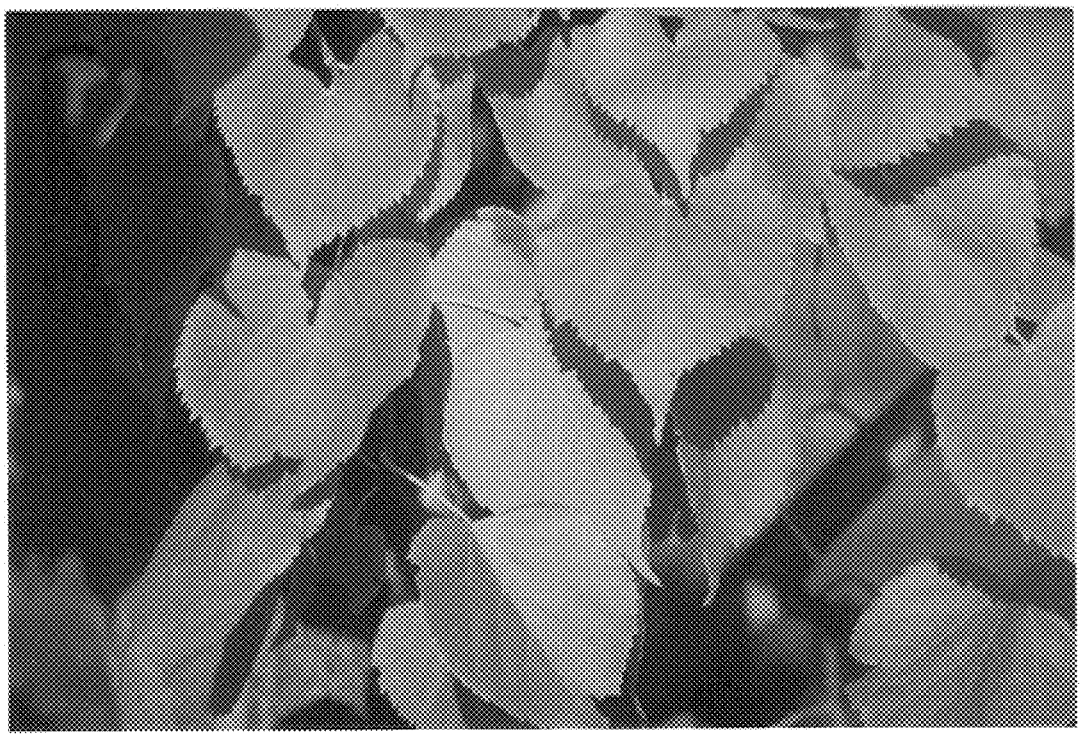
FIG. 4 illustrates during the fall of 1998 typical foliage of the new cultivar formed on a budded tree of the new cultivar having an age of approximately 10 years. The attractive consistent fall yellow leaf coloration is apparent.

*Fall color.*—Attractive golden yellow, Green-Yellow Group 1A (see FIG. 4).

*Maturity.*—The foliage changes color in the fall ahead of all known *Tilia cordata* cultivars, such as 'Glenleven' (non-Patented in the United States) and 'Greenspire' (U.S. Plant Pat. No. 2,086) and approximately one week behind *Tilia americana*. Fall coloration commonly begins during the first week of October and was at its peak on October 5th during 2000.

*One year-old dormant winter twigs.*—Greyed-Orange Group 164A.

*Two year old dormant winter twigs.*—Grey-Brown Group 199A, and Grey-Brown Group 199B when fully mature.

*Buds.*—Yellow Group 2A during early fall and assume a winter coloration of Greyed-Orange Group 175A. Accordingly, the gold-colored buds of late summer turn to brown in the winter

*Bud scales.*—Commonly there are three exposed bud scales

Flowers: Fragrant and very low in frequency. When formed, the flowers appear at a time similar to that of the 'Ronald' Linden cultivar. Seed production tends to be sparse to nil. Flowers have not formed during the past three years and accordingly detailed information concerning the appearance of the flowers and seeds is not available.

Resistance: Resistance is good to leaf gall mites and fungal leaf spotting. Such characterization of resistance was based on general field observations. The new cultivar was selected over hundreds of other crosses and seedlings in view of its resistance to leaf gall mites and fungal leaf spotting. At the growing location leaf gall mites occur every year and are present every year on the susceptibel plants. Fungal leaf spotting also is commonly observed in *Tilia cordata* trees growing in the area. During 2000 the new cultivar of the present invention was the only Linden cultivar out of many grown in the area not to experience fungal leaf spotting.

We claim:

1. A new and distinct *Tilia cordata*×*Tilia mongolica* Linden tree cultivar which exhibits the following combination of characteristics:

(a) Exhibits an upright crown which renders it particularly well suited for growing in a setting where a reduce crown spread is desired, (b) Forms attractive glossy medium green foliage during the summer and consistent golden yellow foliage in the fall that displays good resistance to leaf gall mites and fungal leaf spotting, (c) Forms attractive exfoliating grey-brown bark once the tree reaches a caliper of approximately two inches, (d) Forms on a moderate basis fragrant flowers and a sparse seed crop, and (e) Exhibits superior winter hardiness and a high degree of tolerance to winter sunscald damage; substantially as illustrated and described.

* * * * *